United States Patent
Sawamura et al.

(10) Patent No.: US 12,384,831 B2
(45) Date of Patent: Aug. 12, 2025

(54) FUSION PROTEIN AND HIGH-DENSITY LIPOPROTEIN MEASUREMENT KIT USING SAME

(71) Applicant: Tatsuya Sawamura, Matsumoto (JP)

(72) Inventors: Tatsuya Sawamura, Matsumoto (JP); Akemi Kakino, Matsumoto (JP)

(73) Assignee: Tatsuya Sawamura, Nagano (JP)

( * ) Notice: Subject to any disclaimer, the term of this patent is extended or adjusted under 35 U.S.C. 154(b) by 1277 days.

(21) Appl. No.: 16/970,225

(22) PCT Filed: Feb. 13, 2019

(86) PCT No.: PCT/JP2019/005007
§ 371 (c)(1),
(2) Date: Aug. 14, 2020

(87) PCT Pub. No.: WO2019/159934
PCT Pub. Date: Aug. 22, 2019

(65) Prior Publication Data
US 2022/0089686 A1     Mar. 24, 2022

(30) Foreign Application Priority Data
Feb. 14, 2018  (JP) .................. 2018-024007

(51) Int. Cl.
G01N 33/92      (2006.01)
C07K 14/705     (2006.01)
C07K 14/775     (2006.01)
C07K 16/28      (2006.01)
G01N 1/28       (2006.01)
G01N 33/68      (2006.01)

(52) U.S. Cl.
CPC ............ *C07K 14/775* (2013.01); *C07K 16/28* (2013.01); *G01N 1/28* (2013.01); *G01N 33/6893* (2013.01); *C07K 2317/92* (2013.01); *C07K 2319/30* (2013.01); *G01N 2001/2893* (2013.01); *G01N 2496/00* (2013.01); *G01N 2800/044* (2013.01)

(58) Field of Classification Search
CPC .. C07K 14/775; C07K 16/28; C07K 2317/92; C07K 2319/30; C07K 14/705; C07K 16/18; C07K 2319/00; C07K 16/40; G01N 1/28; G01N 33/6893; G01N 2001/2893; G01N 2496/00; G01N 2800/044; G01N 33/92; G01N 2800/226; G01N 2800/32; G01N 2800/323
See application file for complete search history.

(56) References Cited

U.S. PATENT DOCUMENTS

2013/0017556 A1   1/2013  Pritchard Jr.

FOREIGN PATENT DOCUMENTS

| | | |
|---|---|---|
| JP | 2012-100585 A | 5/2012 |
| JP | 2015-010879 A | 1/2015 |
| WO | 03/014145 A2 | 2/2003 |

OTHER PUBLICATIONS

Lee et al. ("Antibody Production with Synthetic Peptides", Methods Mol. Biol., 2016; vol. 1474, pp. 25-47) (Year: 2016).*
Uniprot (print retrieved Dec. 1, 2023, https://www.uniprot.org/uniprotkb/P04114/entry). (Year: 2023).*
Iwamoto et al., "An Alternative Protein Standard to measure Activity of LOX-1 Ligand Containing ApoB (LAB)—Utilization of Anti-LOX-1 Single-Chain Antibody Fused to apoB Fragment," Journal of Atherosclerosis and Thrombosis, 2011, vol. 18, No. 9, pp. 818-828.
Besler et al., "Mechanisms underlying adverse effects of HDL on eNOS-activating pathways in patients with coronary artery disease," The Journal of Clinical Investigation, Jul. 2011, vol. 121, No. 7, pp. 2693-2708.
Huang et al., "An abundant dysfunctional apolipoprotein A1 in human atheroma," Nat Med., Feb. 2014, vol. 20, No. 2, pp. 193-203.
Kakino et al., "A Novel method to Quantify the Biological Activity of Modified HDL," International Symposium on Ahterosclerosis (ISA) 2018 Abstracts, Jun. 2018, vol. 32, p. 35.
Apr. 23, 2019 International Search Report issued in International Patent Application No. PCT/JP2019/005007.
Nov. 8, 2021 Extended Search Report issued in European Patent Application No. 19753706.1.
Jul. 20, 2022 Office Action issued in Chinese Patent Application No. 201980013331.X.
Kakino, Akemi et al.; "A Novel Cell-Free, Non-Fluorescent Method to Measure LOX-1-Binding Activity Corresponding to The Functional Activity of HDL"; J Atheroscler Thromb; vol. 26; No. 11; Apr. 3, 2019; pp. 947-958.

* cited by examiner

*Primary Examiner* — Gregory S Emch
*Assistant Examiner* — Nam P Nguyen
(74) *Attorney, Agent, or Firm* — Oliff PLC

(57) ABSTRACT

A fusion protein being a lipid-free reference standard having good long-term storability, which is used for measuring the quantity or quality of modified HDL, and a method for accurately, repeatability and reliably measuring high-density lipoprotein using the same. In the fusion protein, a complete protein sequence or partial fragment protein sequence for ApoA I is linked directly or via a spacer to a LOX-1 binding protein sequence that binds to a lectin-like oxidized LDL receptor: LOX-1. The method for measuring a modified high-density lipoprotein in a test sample is a method for measuring a modified high-density lipoprotein through binding of the modified high-density lipoprotein to LOX-1 and an anti-APOA I antibody, wherein, using the fusion protein as a reference standard for the modified high-density lipoprotein, the modified high-density lipoprotein in the test sample is determined by comparison with the reference standard through optical detection and/or radiation dosage detection.

7 Claims, 4 Drawing Sheets

Specification includes a Sequence Listing.

Fig. 1

IgK leader → V_H →

MDFGLIFFIVALLKGVQCEVKLLESGGGLVQPGGSLKLSC

AVSGFDFSRYWMSWVRQAPGKGLEWIGEINPDSSTINFTP

SLKDKFIVSRDNAKNTLYLQMSKVRSEDTALYYCARNDVL

Linker → V_L →

LGAMDYWGQGTSVTVSSGGGGSGGGGSGGGGSDVLMTQTP

LSLPVSLGDQASISCRSSQTIVHSNGKTYLEWYLQKPGQS

PKLLIYKVSNRFSGVPDRFSGSGSGTDFTLKISRVEAEDL

Linker →

GVYYCFQGSHVPLTFGAGTKLELKGGGGSGGGGSGGGGSP apoA1 (31aa-) →

WDRVKDLATVYVDVLKDSGRDYVSQFEGSALGKQLNLKLL

DNWDSVTSTFSKLREQLGPVTQEFWDNLEKETEGLRQEMS

KDLEEVKAKVQPYLDDFQKKWQEEMELYRQKVEPLRAELQ

EGARQKLHELQEKLSPLGEEMRDRARAHVDALRTHLAPYS

DELRQRLAARLEALKENGGARLAEYHAKATEHLSTLSEKA

KPALEDLRQGLLPVLESFKVSFLSALEEYTKKLNTQ SEQ ID NO:1

-[V5]-[6xHis]

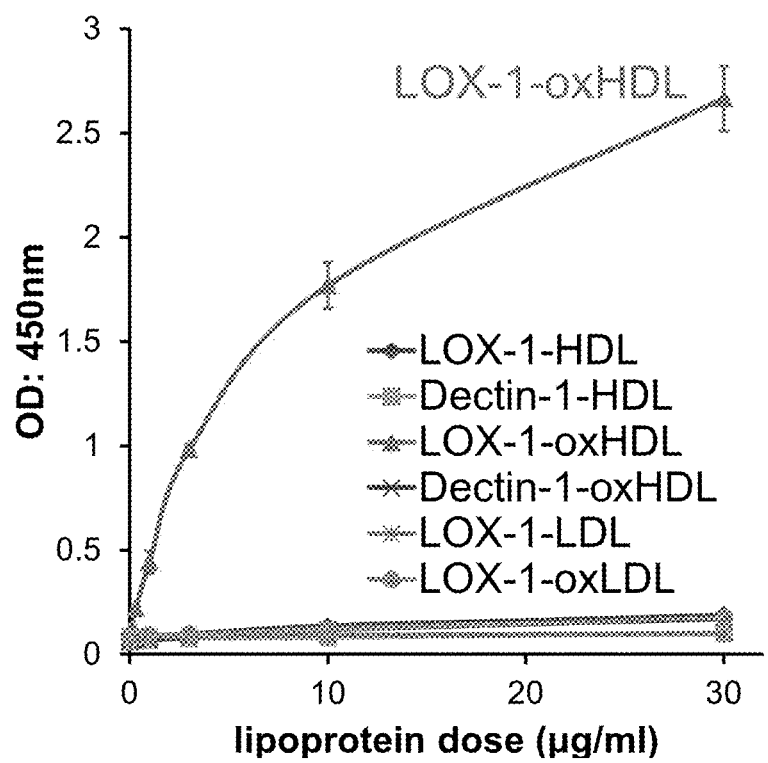

FUSION PROTEIN AND HIGH-DENSITY LIPOPROTEIN MEASUREMENT KIT USING SAME

The present application contains a Sequence Listing that has been submitted electronically in ASCII format and is hereby incorporated by reference in its entirety. The ASCII copy, created on Apr. 28, 2021, is named Substitute Sequence Listing_ST25.txt and is 6,345 bytes in size.

TECHNICAL FIELD

The present invention relates to a fusion protein used for a reference standard for measurement of a modified high-density lipoprotein; and nucleic acids, a vector or cells for forming thereof; and a measurement method or a measurement kit for the modified high-density lipoprotein.

BACKGROUND OF THE ART

Blood cholesterol includes so-called good cholesterol (i.e. High Density Lipoprotein: HDL) and so-called bad cholesterol (i.e. Low Density Lipoprotein: LDL). Concentrations of them in the blood are generally used as indexes for medical check-ups as well as a concentration of neutral fats.

Principle components of HDL are intrinsically ApoA I as a main constitute protein and a phospholipid. The HDL not only inhibits to oxidation of LDL, but also reduces cytotoxicity by oxidized LDL through increasing NO. Further it achieves an antiarteriosclerotic effect. It is known that modified HDL exists with high concentration in the blood of an arteriosclerosis patient. Non-patent document 1 discloses the modified HDL increases in the coronary artery disease patient, and it influences on blood vessels through LOX-1.

It has come to understand that the modified HDL loses the antiatherosclerotic effect which HDL originally has, and is important for pathogenesis or progression of the atherosclerosis. Non-patent document 2 disclosed that modified ApoA I as apoprotein of HDL is abundantly accumulated in a human atherosclerotic plaque.

It seems that the modified HDL is very significant in a human pathophysiology, because measurement results thereof are obtained from actual patients. Accordingly, the modified HDL among the good cholesterols may be pathogenesis for various diseases such as the arteriosclerosis etc. Therefore it is necessary to determine not only an amount of HDL but also quantity or quality of the modified HDL.

As a method for measuring the modified HDL of the prior arts, a measurement method for determining it by an anti-modified HDL antibody is known. An amount of specific epitopes, which the antibody recognizes, can be merely detected. Since the amount of the epitopes can be just determined, there are some problems in which the essential modified HDL with various modifications cannot be detected as the same time as the detection of the epitopes and while reflecting bioactivity thereof.

And there is the other problem for a reference when preparing the calibration curve for measurement thereof. For example, when the modified HDL with 4-hydroxynonenal (HNE) is determined, HNE-fodified HDL is used as the reference thereof. And when modified HDL with malondialdehyde (MDA) is determined, MDA-modified HDL is used as the reference thereof. Therefore, when the modified HDL with the various modifications is determined by a single measurement method, it is substantially impossible to determine it because not only the antibodies thereof are different but also the references thereof vary. In order to solve this problem, a method for oxidation of HDL under presence of copper ions etc. is known (hereunder it is also termed as oxidized HDL). However, the oxidized HDL and the modified HDL prepared by modification with HNE or MDA are unstable and cannot be stored for long time because of instability. And the calibration curve must be prepared every measurement thereof because of the instability. Further, since they are easy to generate a quality variation among their lots, it is impossible to prepare them with reproducibility in order to measure it. Accordingly, it is necessary to correct the measurement results in the light of difference among the lots of the reference standard, and there are some problems of accuracy thereof. Consequently, if the real concentrations of the modified HDL in the test samples are equal, it is difficult to obtain constant measurement values during the long term tests, on the large scale tests or among the measurement tests and the measurements include the problems of credibility of meanings which the measurement values indicate themselves.

PRIOR ART DOCUMENT

Non-Patent Document

[Non-patent Document 1] Besler C et al.: "Mechanisms underlying adverse effects of HDL on eNOS-activating pathways in patients with coronary artery disease.", J Clin Invest., Vol. 121, p. 2693-2708, 2011

[Non-patent Document 2] Huang Y et al.: "An abundant dysfunctional apolipoprotein A1 in human atheroma.", Nat Med, Vol. 20, p. 193-203, 2014

SUMMARY OF THE INVENTION

Problems to be Solved by the Invention

The inventors made intensive studies to solve the above-mentioned problems. As a result of the intensive studies, it has been found that the modified HDL with the various modifications can be determined by measuring HDL which is simultaneously recognized by LOX-1 and an anti-ApoA I antibody, and that a fusion protein in which ApoA 1 is fused with a protein being able to specifically bind LOX-1 such as LOX-1 binding sites of an antibody against LOX-1 (i.e. anti-LOX-1 antibody) indicates specific binding properties as well as the modified HDL against LOX-1 and the anti-ApoA I antibody and further the fusion protein can be used for the stable reference standard. Accordingly, the inventors achieve the present invention.

The present invention was made in view of solving the above described problems, and its object is to provide a fusion protein, that is used for determining quality of HDL because HDL as the good cholesterol may include the modified HDL which influences to develop and progress arteriosclerosis and is used for determining bioactivity by measuring binding-activity to a receptor while substantially recognizing the modified HDL with the various modification and that does not include a lipid and can be stored for long time and can act as a reference which is able to be prepared with reproducibility and can enhance the credibility by reducing variations among the measurement tests. And other objects are to provide nucleic acids, a vector and cells which form the fusion protein, and a method or a kit for accurately, repeatability and reliably measuring high-density lipoprotein which is recognized by LOX-1 and the anti-ApoA I antibody.

Means for Solving Problems

A fusion protein of the present invention developed to achieve the objects described above is characterized in that a complete protein sequence or partial fragment protein sequence for an apolipoprotein A1: ApoA I is linked directly or via a spacer to a LOX-1 binding protein sequence for binding to a lectin-like oxidized LDL receptor: LOX-1.

For example, in the fusion protein, the LOX-1 binding protein sequence is an anti-LOX-1 antibody or a LOX-1 binding domain sequence thereof.

In the fusion protein, the anti-LOX-1 antibody or the LOX-1 binding domain sequence may have an active site to an antibody for binding to LOX-1 by an antigen-antibody reaction.

In the fusion protein, the active sites of the anti-LOX-1 antibody may be an active site of a Fv type antibody.

In the fusion protein, it is preferable that the partial fragment protein sequence for ApoA I includes regions of amino acid numbers: 31-267aa of human ApoA I.

Nucleic acids of the present invention developed to achieve the objects described above are characterized in that it codes the above-mentioned fusion protein.

A vector of the present invention developed to achieve the objects described above is characterized in that the above-mentioned nucleic acids are introduced thereinto.

Cells of the present invention developed to achieve the objects described above have the above-mentioned vector.

The present invention of a method for measuring a modified high-density lipoprotein in a test sample, which is developed to achieve the objects described above, is characterized in that it is the method for measuring the modified high-density lipoprotein through binding of the modified high-density lipoprotein to LOX-1 and an anti-APOA I antibody, wherein, using the fusion protein according to any one of claim 1-3 as a reference standard for the modified high-density lipoprotein, the reference standard and the modified high-density lipoprotein in the test sample are determined by comparison with the reference standard through optical detection and/or radiation dosage detection.

The invention of a measurement kit for a modified high-density lipoprotein, which is developed to achieve the objects described above, is characterized in that the modified high-density lipoprotein is measured through bonding the modified high-density lipoprotein to LOX-1 and the anti-APOA I antibody, wherein using the fusion protein as the reference standard of the modified high-density lipoprotein, and it is measured through optical detection and/or radiation dosage detection.

The measurement kit for the modified high-density lipoprotein is used for measuring the quantity or quality of the modified high-density lipoprotein in a test sample by comparison with the reference standard through the optical detection and/or radiation dosage detection.

It is preferable that the measurement kit for the modified high-density lipoprotein further comprises LOX-1 and/or an anti-ApoA I antibody.

In the measurement kit for the modified high-density lipoprotein, the test sample is whole blood, plasma or serum.

Effects of the Invention

The fusion protein of the present invention is used for a universal reference standard as a measurement reference to measure quality of the modified HDL, because HDL as the good cholesterol may include the modified HDL which influences to develop and progress arteriosclerosis.

The fusion protein is an artificial fusion recombinant protein without having lipid, which can be stored for long time and can be prepared with reproducibility. And the fusion protein is the reference standard which is used for obtaining the measurement values having the credibility towards the testing samples such as the whole blood took from human and the plasma or the serum obtained through the treatment thereof by reducing the variations among the measurement samples and enhancing reliability even if the measurement date and time are different.

The prior measurement of the modified lipid has some problems. It is not easy to determine the modified lipid because of instability of the lipid. And it is necessary to treat the testing samples quickly. Although the problems of the instability of the testing samples may be solved by optimizing the storing method thereof or by shortening the measurement time, the other problem with no guarantee for reliability and repeatability of the measurement because of instability of the reference standard as the reference for the measurement cannot be solved. The fusion protein is a stable reference standard, which has no lipid and can be reproducibly prepared by recombinant DNA technique for an artificial protein having affinities to both being measured of a LOX-1 protein and an anti-ApoA I antibody.

The fusion protein is timely prepared with the same quality by using the nucleic acids for forming the fusion protein, the vector in which the nucleic acids are introduce, or the cells such as animal cells having the vector.

The method for measuring the modified high-density lipoprotein of the present invention by using the fusion protein is a measurement method with substrate-specificity by using LOX-1 which binds the modified HDL. The method for measuring it is extremely simple because the modified HDL with the various modifications can be detected and determined by using the same procedures.

Generally, the modified HDL actually includes various kinds of modified HDL. Although that is not the case that they are simultaneously determined, it is important how the modified HDL actually contributes to bioactivity thereof. According to the method for measuring the modified high-density lipoprotein, the amount and quality of the modified HDL can be detected and measured by using the binding ability of a LOX-1 receptor to the various modified HDL and by using an evaluation capability of the bioactivity based on the binding degree to the LOX-1 receptor.

In the method for measuring it, the fusion protein is used for the reference standard which is a control for measurement of quantitative determination or quality determination thereof. According to the method for measuring it, the fusion protein is used for LOX-1 recognition sites where the variable region of the anti-LOX-1 antibody as the LOX-1 binding protein is focused. The chimeric protein of this protein and ApoA I protein is prepared, and then the modified HDL in the test sample is determined by using the chimeric protein.

According to the method for measuring it, various epitopes can be simultaneously recognized towards the modified HDL. The method for measuring it is used for determining the bioactivity of the modified HDL by the binding activity of the receptor. Therefore the amount and quality of the modified HDL are measured accurately, repeatability and reliably.

And according to the present invention of the measurement kit for the modified high-density lipoprotein which is used for the method for measuring it, the amount and quality of the modified HDL can be simply and expeditiously determined accurately, repeatability and reliably. The kit is useful for checkup and prognosis of various cardiac diseases and ischemic diseases including the arterioscle or thrombosis, and assists the prevention of those diseases.

The measurement kit, which can assess the activity of the lipoprotein including ApoA I that binds LOX-1 after Immobilization of LOX-1 by ELISA (Enzyme-Linked Immunosorbent Assay) for a receptor binding assay, can be used for general purposes.

BRIEF DESCRIPTION OF DRAWINGS

FIG. 1 is a figure which indicates an amino acid sequence of the fusion protein of the present invention by single character codes.

FIG. 2 is a figure which indicates a graph of the results of tests whether LOX-1 or Dectin-1 binds HDL, oxidized HDL, LDL and oxidized LDL or not.

MODE FOR CARRYING OUT THE INVENTION

Figure 3:
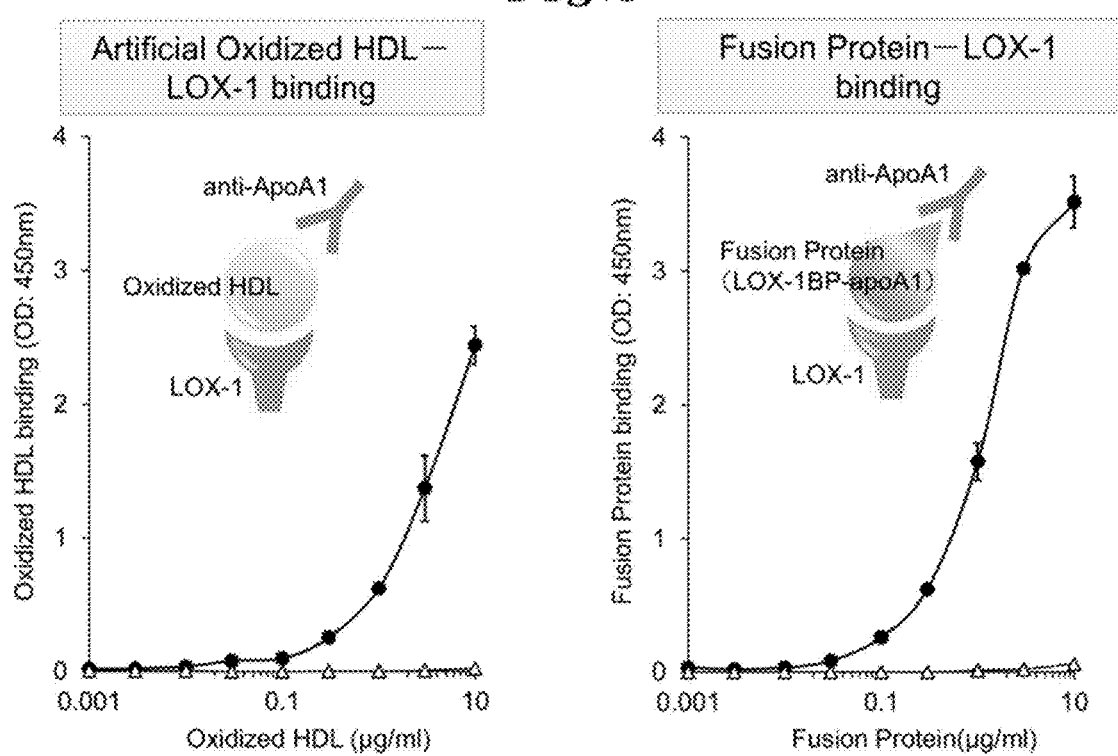
FIG. 3 is a figure which indicates graphs of comparisons of the results of tests of binding between the fusion protein applying the present invention and LOX-1, and binding between the artificial oxidized HDL not applying the present invention and LOX-1.

Hereunder, embodiments to practice the present invention be explained in detail will, but the scope of the present invention is not restricted by these embodiments.

The fusion protein of the present invention is a chimeric protein, in which a complete protein sequence or a partial fragment protein sequence of ApoA I combines with a LOX-1-binding protein sequence that binds to LOX-1 directly or via a spacer.

Therefore, the fusion protein has a specific binding property to LOX-1 and another specific binding property to the anti-ApoA I antibody. For example, when determining the modified HDL through the sandwich immunoassay by using LOX-1 and the anti-ApoA I antibody, the fusion protein can be used as the reference standard which is stable and easy to control the accuracy instead of the prior reference standard (artificial oxidized HDL).

The fusion protein is stable, because it does not include the lipid. And the fusion protein can be manufactured in a large scale by the recombinant DNA technology, and can be obtained as the same lot of the reference standard in a large quantity.

When the fusion protein has the partial fragment protein sequence as a smaller molecule than the complete protein sequence of the full length of ApoA I, the fusion protein is easier to be prepared by the recombinant DNA technology than protein having the complete protein sequence.

In the fusion protein, for example, the LOX-1-binding protein sequence is the LOX-1-binding domain sequence which is the anti-LOX-1 antibody or a part thereof and may bind LOX-1 specifically. It is exemplified with the antibody and the immunoglobulin Ig which relates to the structure or the function thereof. The immunoglobulin Ig is not restricted with the isotype class or sub class. It is exemplified with IgG such as IgG1, IgG2 and IgG3 etc., IgM, IgA, IgD, and IgE etc.

When the LOX-1-binging protein sequence is the anti-LOX-1 antibody consisting of full length of the immunoglobulin Ig, it is not restricted so long as it is the antibody which binds to LOX-1. It may be originated from any animals such as human, mouse or bovine etc. Concretely, it is exemplified with mouse anti-LOX-1 monoclonal antibody #10-1 which specifically binds to human LOX-1 (see "LOX-1-MT1-MMP axis is crucial for RhoA and Rac1 activation induced by oxidized low-density lipoprotein in endothelial cells.", Sugimoto K., et al., Cardiovasc Res, Vol. 84, p124-136, 2009).

When the LOX-1-binding protein sequence is a LOX-1-binding domain sequence which is a part of the anti-LOX-1 antibody as a functional fragment of the antibody including a variable region of the immunoglobulin, it is exemplified with $V_H$, $V_L$, Fv, Fab and $F(ab')_2$.

In the fusion protein, for example, the anti-LOX-1 antibody or LOX-1-binging domain sequence may have an active site for the antigen which binds to LOX-1 by an antigen-antibody reaction, preferably an active site for a Fv type antigen. The Fv type antigen (scFv, $V_H$–$V_L$) is a functional fragment for the antigen in which a heavy chain variable region ($V_H$) and a light chain variable region ($V_L$) are combined, as shown in FIG. 1.

The complete protein sequence or partial fragment protein sequence of ApoA I in the fusion protein is not restricted so long as it acts as ApoA I. For example, it may be originated from any animals such as human, mouse or bovine etc.

A concrete example of the fusion protein is indicated by the single character codes as shown in FIG. 1, and by three character codes as shown in SEQ ID NO:1. The fusion protein has the LOX-binding domain (broken line parts) of the anti-LOX-1 antibody (#10-1) as the LOX-1-binding protein sequence which binds to LOX-1 and the region of Amino acid Nos. 31-267aa in human ApoA I which is the anti-ApoA I antibody binding protein as the partial fragment protein sequence of ApoA I.

The LOX-1-binding protein sequence which binds to LOX-1 or the complete protein sequence or partial fragment protein sequence of ApoA I in the fusion protein is not restricted to ones originated from nature. It may be a mutant protein in which parts of amino acids are substituted, deleted or inserted so long as the functions thereof are expressed.

In the fusion protein, a C-terminal side of the complete protein sequence or partial fragment protein sequence of ApoA I may be bound to be connected to a N-terminal side of the LOX-1-binding protein sequence. Or a N-terminal side of the complete protein sequence or partial fragment protein sequence of ApoA I may be bound to be connected to a C-terminal side of the LOX-1-binding protein sequence. They may be directly bound to be connected through amide bonds, may be indirectly bound to be connected through amide bonds via a spacer group as polypeptide which does not inhibit the action of ApoA I and LOX-1, or may be indirectly bound to be connected through covalent bonds such as ether bonds etc. except for amide bonds via a spacer group as polypeptide and/or non-polypeptide.

The fusion protein, which applies the present invention, is compared with the oxidized HDL-including protein, which does not apply the present invention. The fusion protein differs from the prior oxidized HDL, which is improper for the reference or the reference standard because the oxidized lipid is unstable. The fusion protein is a protein which is substituted by the artificial protein instead of the oxidized HDL. Since the fusion protein does not have a phospholipid, it is stable and can be prepared with reproducibility.

The method for manufacturing the fusion protein is not particularly restricted. The fusion protein may be prepared through the well-known genetic technology, or may be prepared through the chemical synthesis.

For example, the following genetic technology can be performed. The nucleic acids, which code the fusion protein, are prepared. After the vector, in which the nucleic acids are introduced, is prepared, the fusion protein is produced from the host cells by using the vector. For example, the host cells are exemplified with animal cells such as COS cells and CHO cells, and bacteria such as yeast and *Escherichia coli* etc.

The outline of the production of the fusion protein of an embodiment will be explained in detail. The fusion protein is produced from the anti-LOX-1 antibody and human ApoA I as the anti-ApoA I antibody-binding protein.

Concretely, the fusion protein is obtained from DNA for coding LOX-1-binding protein sequence which binds to LOX-1 (ex. full length of a complete amino acid sequence of the anti-LOX-1 antibody or its partial fragment as an amino acid sequence which binds to LOX-1) and DNA for coding full length of a complete protein sequence of the ApoA I or its partial fragment as a partial fragment protein sequence which binds to the anti-ApoA I antibody through PCR procedures based on the known nucleotide sequence information from an anti-LOX-1 antibody and ApoA I, or is obtained through the chemical synthesis.

After that, DNA for coding the LOX-1-binding protein moiety and the DNA for coding the full length or partial fragment of ApoA I are combined to match their frame so as to prepare a chimeric gene for coding the fusion protein.

Then, the chimeric gene is appropriately introduced into the vector such as *Escherichia coli* plasmid by using a restriction enzyme and a ligase enzyme to prepare the recombinant vector as the fusion protein-expressing vector. Hereunder, the outline of the recombinant vector will be explained.

The recombinant vector is introduced into the host cells to become transformed, and thereby the recombinant cells as the fusion protein-expressing cells.

And then, the recombinant cells are cultured. The fusion protein is purified and collected from the culture by an adequate isolation method such as centrifugal separation, salting-out, centrifugal separation and chromatography as affinity chromatography.

The fusion protein as the reference standard is used for the the method for measuring the modified high-density lipoprotein in the test sample. In the method, the modified high-density lipoprotein is determined by using a reaction in which the modified high-density lipoprotein is specifically bound to LOX-1 and the anti-ApoA I antibody.

Concretely, the method has the following procedures. (1) By using the fusion protein as the reference standard, the calibration curve, the contrast table or the conversion equation etc. as the reference for the correlative relationship between the concentration or activity thereof and measured values such as optical strength or radiation dosage etc. is prepared. For example, after the standard solutions of the fusion protein are prepared by the phased dilution thereof, the immunoassay for them is performed. And then the measurement values of the optical strength such as the absorbency or the radiation dosage such as the radiation strength of each concentration of the standard solutions are determined, and the calibration curve or the contrast table etc. between the concentration of the fusion protein and the measurement values of the standard solutions.

(2) On the other hand, the modified HDL in the test sample such as the human whole blood, plasma or serum is measured. For example, the immunoassay is performed as well as the measurement for the standard solutions, and then the measurement value of the optical strength or the radiation dosage etc. of the modified HDL in the test sample is obtained.

(3) The amount and quality of the modified HDL can be inclusively detected and determined by comparison of the measurement value of the optical strength or the radiation dosage of the modified HDL with the calibration curve or the contrast table etc. or by assignment of the measurement value into the conversion equation. For example, the measurement value of the optical strength or the radiation dosage of the modified HDL may be turned into the calibration curve or contrast table or may be assigned into the conversion equation to obtain the corresponding value for the fusion protein as the relative value of the amount and quality of the modified HDL towards the fusion protein. The measurement value may be assigned into the conversion equation estimated from the calibration curve or from the contrast table to calculate the corresponding value of the fusion protein.

For the method for measuring the modified high-density lipoprotein, the immunoassay using LOX-1 and the anti-ApoA I antibody is preformed. The immunoassay is performed by well-known procedures such as the sandwich ELISA and competitive ELISA.

The method for measuring the modified high-density lipoprotein is performed for measuring the test sample, for example, through so-called solid phase method, in which one of LOX-1 and the anti-ApoA I antibody is immobilized on the support body. Examples of the support body are respective wells of the microplate, and/or beads.

In the method for measuring the modified high-density lipoprotein, the immunoassay for using LOX-1 and the anti-ApoA I antibody can be performed instead of the prior oxidized HDL measurement method using the oxidized HDL as the reference for measurement, or can be additionally performed with it.

The method for measuring the modified high-density lipoprotein is explained by the following example of solid phase procedure of LOX-1 on the support body such as the wells of the microplate etc. The test sample such as the whole blood, plasma or serum obtained from human is applied onto the wells, and the modified HDL included in the test sample is caught on LOX-1. And then, the labeled anti-ApoA I antibody are subsequently or preliminarily added thereto to make the antibody bind to the modified HDL caught. The modified HDL in the test sample is determined through the optical detection procedure and/or the radiation dosage detection procedure by using the label of the bound anti-ApoA I antibody as the index.

The label is used for measurement through the optical detection procedure and/or the radiation dosage detection procedure. For example, examples thereof are enzymes (for enzyme-immunoassay, EIA, ELISA), fluorescent materials (for fluorescent-immunoassay, FIA), radioactive materials (for radio-immunoassay, RIA) etc.

The labeled secondary antibody which binds to the anti-ApoA I antibody may be used while the anti-ApoA I antibody is not labeled, instead of using the labeled anti-ApoA I antibody. The anti-ApoA I antibody may be the monoclonal antibody or the polyclonal antibody.

LOX-1 can be prepared through well-known procedures (for example, JPH09-98787A). The anti ApoA I antibody may be commercially available.

The modified HDL, which can be measured through the method for measuring the modified high-density lipoprotein, is exemplified with HCIO-HDL, HNE-HDL, Carbamylated HDL and MDA-HDL. Those modified HDLs impair the vascular endothelial cells on the blood vessel walls. They increase the risk of development of various diseases such as cardiovascular diseases which cause arteriosclerosis or thrombogenesis and arteriosclerotic diseases as ischemic disease.

The method for measuring the modified high-density lipoprotein can be used for obtaining indexes, for example, a risk evaluation index for arteriosclerotic diseases, especially evaluation index such as strong relationship between brain infarctions and it or relevance between intimal hypertrophy in arteria carotis, surrogate markers for development of the arteriosclerosis and judgment index for therapeutic effect of the arteriosclerosis, and can be used for diagnoses, selection of medical treatments or digitalization of results of clinical examinations.

According to the method for measuring the modified high-density lipoprotein, the amount or quality of the modified HDL, which is never determined by only medical checkup of mere measurement results of HDL and LDL, can be measured. If necessary, the method can provide an appropriate assessment of the modified cholesterol or a medical treatment with the measurement of the modified LDL.

The method for measuring the modified high-density lipoprotein can be performed by using the measurement kit for the modified high-density lipoprotein of the present invention, by which the modified high-density lipoprotein binds to LOX-1 and the anti-ApoA I antibody.

The measurement kit for the modified high-density lipoprotein can be used for preparing the calibration curve, the contrast table or the conversion equation etc. after optically measuring the optical strength of each concentration of the fusion protein while the fusion protein is used for the reference standard of the modified high-density lipoprotein. On the other hand, when the measurement kit for the modified high-density lipoprotein can be used for measuring the modified HDL in the test sample such as the human whole blood, plasma or serum, the optical strength thereof is optically measured through the so-called solid phase method in which any one of LOX-1 and the anti-ApoA I antibody is immobilized on the support body such as the respective wells of the microplate and/or the beads and another of LOX-1 and the anti-ApoA I antibody is added and then it is compared with the calibration curve or the contrast table etc. or is applied into the conversion equation in order to obtain the concentration of the modified HDL in the test sample by detection and measurement thereof.

In the measurement kit for the modified high-density lipoprotein, LOX-1 is immobilized on the support body such as the wells of the microplate if necessary. The measurement kit has the fusion protein which binds to it, the anti-ApoA I antibody which binds to the fusion protein, and a buffer. Or in the measurement kit, LOX-1 is immobilized on the other support body such as the wells of the microplate, on which the test sample for measuring the modified HDL can be added. And the measurement kit has the buffer, and the anti-ApoA I antibody which binds to it when the modified HDL binds to the LOX-1. The anti-ApoA I antibody is labeled or is not labeled, and co-exists with the secondary label.

EMBODIMENTS

Hereunder, details of embodiments of the fusion protein of the present invention, the measurement kit for the modified high-density lipoprotein using the same, and the method for measuring the modified high-density lipoprotein after preparing the kit and using it, will be described.

First of all, the fusion protein of the present invention was prepared as follows.

(Preparation Example 1) Preparation of Fusion Protein

In order to obtain a protein having affinities for both of the LOX-1 protein and the anti-ApoA I antibody, firstly the fusion protein gene consisting of the anti-LOX-1 antibody gene (the variable region (i.e. Fv region)) and the ApoA I gene was prepared. The anti-LOX-1-Fv gene as the Fv-type antibody gene was used. It was prepared based on the variable region gene which was cloned from cDNA of the hybridoma producing the mouse monoclonal anti-human-LOX-1 antibody (#10-1) (see "LOX-1-MT1-MMP axis is crucial for RhoA and Rac1 activation induced by oxidized low-density lipoprotein in endothelial cells.", Sugimoto K, et al., Cardiovasc Res, Vol. 84, p127-136, 2009). The ApoA I gene was cloned from cDNA of human liver.

(Preparation Example 1) Cloning of ApoA I Gene

The human ApoA I full length gene (GenBank accession no. NM000039.2; 1,239 bp) as the ApoA I full length gene was obtained through PCR by using the primer set: ApoAI-F (CACCATGAAAGCTGCGGTGCTGACCTTG) (SEQ ID NO:2), ApoAI-R (CTGGGTGTTGAGCTTCT-TAGTGTAC) (SEQ ID NO:3) and PrimeSTAR HS DNA Polymerase (TAKARA #R010A) while using the liver cDNA library of Human MTC Panel II (Clontech) as the template. Next, the full length gene was subjected to subcloning into pcDNA6.2/V5/GW/D-TOPO vector (Invitorgen) by using pcDNA Gateway Directional TOPO Expression kit (Invitrogen). The base sequence was confirmed by using ABI PRISM Cycle sequencing kit (Preparation Example 3) Preparation of Fusion Protein of Fv-Type Anti-LOX-1 Antibody and ApoA I The fusion protein, in which the C-terminal side of the Fv-type anti-LOX-1 antibody and the N-terminal side of ApoA I were combined via the linker sequence, was prepared as the following procedures.

The above-mentioned Fv-type anti-LOX-1 antibody-expressing vector was used as the template. The forward primer (Fv-H-F primer: CACCATGGATTTTGGGCTGAT-TTTTTTTA) (SEQ ID NO:4), the reverse primer (Fv-L-Linker-R primer: ACCAGAGCCGCCGCCGCCGCTAC-CACCACCACCTTTCAACTCCAGCT TGGTCCC) (SEQ ID NO:5) including a part of the linker sequence on 3'-terminal, and PrimeSTAR HS DNA Polymerase (TAKARA #R010A) were used and PCR was performed to re-amplify the Fv-type anti-LOX-1 antibody gene.

And the ApoA I full length gene prepared as above was used as the template. The forward primer (Linker-ApoAI-F primer: AGCGGCGGCGGCGGCTCTGGTGGTGGTG-GATCCCGGCATTTCTGGCAGCAA GATGAAC) (SEQ ID NO:6) having a part of the linker sequence on 5'-terminal, the reverse primer (ApoAI-R primer: CTGGGTGTT-GAGCTTCTTAGTGTACTC) (SEQ ID NO:7) and Prime-STAR HS DNA Polymerase (TAKARA #R010A) were used and PCR was preformed to re-amplify the gene for coding ApoA I.

The Fv-type antibody and ApoA I (55-801 bp) were respectively combined at the C-terminal side of VL and the N-terminal side of ApoA I via the linker sequence, and the fusion protein gene were inserted into pEF6-V5-His vector (Invitrogen) by using an overlap-extension PCR procedure.

Subsequently, KOD-Plus-Mutagenesis Kit (TOYOBO #SMK-101), Linker R primer (GGATCCACCAC-CACCAGAGCCGCCG) (SEQ ID NO:8), ApoA1-31aa F primer (CCCTGGGATCGAGTGAAGGACCTGG) (SEQ ID NO:9) were used, and the amino acid sequence of 19th to 30th including the post-translation cleavage portion Gln24 of ApoA I (see "cDNA cloning of human apoA-I: amino acid sequence of preproapoA-I.", Law S W., et al., Biochem Biophys Res Commun, Vol. 112, p257-264, 1983) was defected. The base sequence was confirmed by using ABI PRISM Cycle sequencing kit. It was used for the protein expression system.

The expression of the fusion protein was performed by using Expi293 Expression System (Invitrogen). The fusion protein, which is secreted in the medium culture, was His-purified by using Ni Sepharose excel resin (GE). After the obtained protein was separated by dialysis in PBS, the filtration sterilization by using a filter having 0.22 μm bore was performed therefor. And it was used for experiments.

(Example 1) Construction of Detecting System for LOX-1-Binding Modified HDL

First of all, 3 mg/ml of the concentration of HDL or LDL, which was separated from the human EDTA plasma by KBr density-gradient centrifugation, was prepared by dilution with PBS. After copper sulfate was added to become 7.5 μM, it was incubated in an incubator under the condition of 37° C. and 5% $CO_2$ for 16 hours. Subsequently, the dialysis for the solution was performed in 0.15 M saline solution including 2 mM EDTA as the extracellular fluid. Thereby, the human oxidized HDL and oxidized LDL were prepared.

It is examined whether the oxidized HDL was bound to the receptor LOX-1 or not through the sandwich ELISA procedure by using the LOX-1 protein and the anti-ApoA I antibody.

Sandwich ELISA Using LOX-1 and Anti-ApoA I Antibody

The recombinant human LOX-1 (61-273aa) or protein Dectin-1 belonging to the same family with LOX-1 for the contrast reference was immobilized on the ELISA plate at 4° C. overnight. After washing with PBS, it was blocked by HEPES buffer including 3% BSA (10 mM HEPES, 150 mM NaCl, pH7.4). After washing PBS three times, oxidized HDL, HDL, oxidized LDL and LDL were respectively added thereto, and they were incubated. After washing with PBS, chicken anti-ApoA I monoclonal antibody (chicken monoclonal anti-ApoB antibody) or HRP-labeled anti-ApoA I polyclonal antibody (sheep polyclonal anti-ApoB antibody-HRP) was added thereto. When chicken anti-ApoA I monoclonal antibody was used, chicken anti-ApoA I monoclonal antibody was added thereto and reacted for 1 hour at room temperature and then it was washed with PBS and secondary antibody: HRP-labeled Donkey anti-chicken IgY was added and incubated for 1 hour at room temperature.

After the antibody response, it was washed with PBS for 5 times. And then, TMB solution was added onto the plate and made it react them at room temperature. After stopping the reaction by 2M sulfuric acid, the absorbency at 450 nm was determined by using SpectraMax 340PC384 (Molecular Devices) to detect the oxidized HDL bound.

The results thereof are shown in FIG. 2. FIG. 2 is a graph of the results in which the binding of HDL, oxidized HDL, LDL and oxidized LDL with LOX-1 or Dectin-1 were detected by the anti-ApoA I antibody in order to investigate whether the detecting system for LOX-1-binding modified HDL can be constructed. As shown in FIG. 2, the binding of oxidized HDL to LOX-1 depended upon the concentration thereof were observed, and the binding of non-oxidized HDL, LDL, and oxidized LDL to LOX-1 were not detected. On the other hand, dectin-1 did not bind to oxidized HDL and also HDL. Herewith, it was found that the modified HDL, which bound to LOX-1, could be detected by ELISA.

(Example 2) Comparison of Artificial Oxidized HDL-LOX-1 Binding and Fusion Protein-LOX-1 Binding The artificial oxidized HDL which was prepared in above-mentioned Example 1, and the fusion protein which was prepared in above-mentioned Preparation Example 1 were respectively used. According to the procedures of above-mentioned Example 1, binding of the artificial oxidized HDL or LOX-1 of the fusion protein with the anti-ApoA I antibody was investigated. The results thereof are shown in FIG. 3 by black circles. As shown in FIG. 3, the prepared fusion protein was simultaneously bound to LOX-1 and the anti-ApoA I antibody. However, as shown in the same figure, when LOX-1 was not immobilized, it was not detected as indicated by outline triangles. Herewith, it was found that the fusion protein can be detected by ELISA as the same procedures for the artificial oxidized HDL.

Incidentally, the artificial oxidized HDL includes the lipid. Since it is easy to be oxidized by the oxygen after the lipid contacts with the air to deteriorate by chemical changes over time, it has poor repeatability thereof. However, when the prepared fusion protein is used, it has excellent repeatability thereof because it does not have the lipid, it is difficult to be oxidized or to cause chemical changes after contacting to the air, it can be kept with high quality thereof. Therefore, according to the measurement by using the fusion protein, and it can be the reference standard for preparing the universal calibration curve, contrast table or conversion equation because it can be a scale for giving the same result usually.

Figure 4:
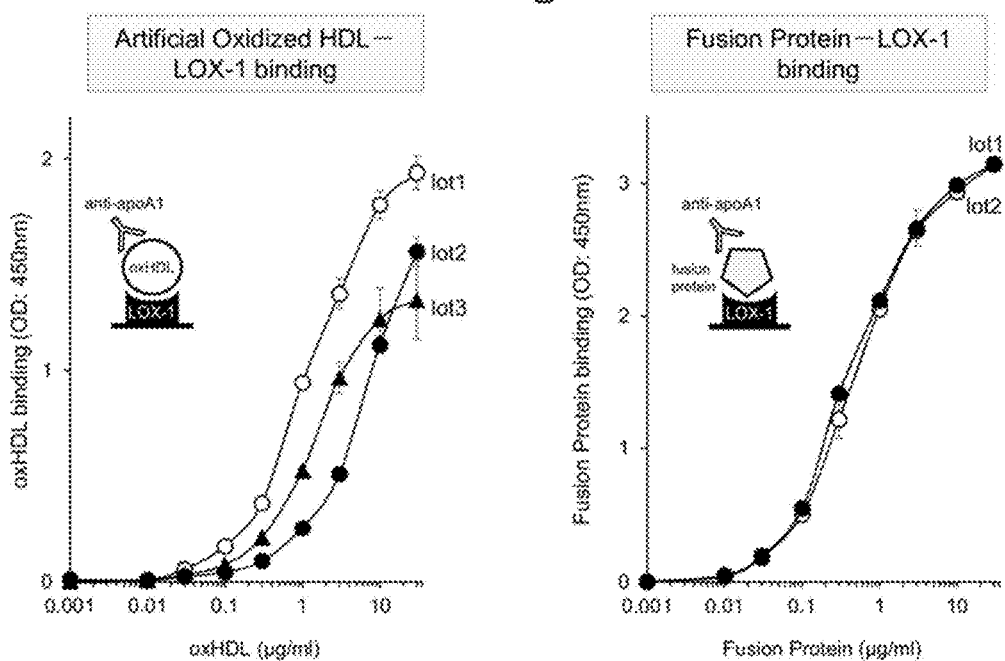
FIG. 4 is a figure which indicates graphs of the results of ELISA of comparisons among lots as regards respective reactivity of the artificial oxidized HDL and the fusion protein to LOX-1.

(Example 3) Comparison of Lots Between Artificial Oxidized HDL and Fusion Protein It was investigated how the difference among the lots of the oxidized HDL, which is prepared by artificial oxidation of HDL corrected from the human plasma, infects the measurement values through the sandwich ELISA (see above-mentioned Example 1) by using LOX-1 and the anti-ApoA I antibody. Also it was similarly investigated how the difference among the lots of the fusion protein of the present invention infects them. And the efficiency of the fusion protein was reviewed. The results thereof are shown in FIG. 4. In the figure, outline circles, black circles and black triangles indicate different lots of the artificial oxidized HDL and the fusion protein. It is found that the three different lots of the artificial oxidized HDL (ox HDL) indicate the different reactivates among of them. On the other hand, it is found that the lots of the fusion protein indicate little difference among of them.

(Example 6) Detection of Modified HDL in Human Blood

According to the procedures of the above-mentioned Example 1, the detection of the modified HDL in the human blood was tried. As the test sample, the samples of EDTA plasma, which were obtained from 6 healthy volunteers, were used.

Figure 5:
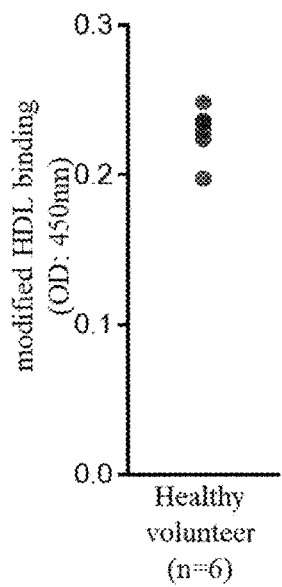
FIG. 5 is a figure which indicates a graph of the results of detection of LOX-1-binding modified HDL in human plasma.

The results thereof are shown in FIG. 5. Namely, it is indicated that the modified HDL in the human blood can be detected through sandwich ELISA by using LOX-1 and the anti-ApoA I antibody.

It is confirmed that the prepared artificial recombinant protein can recognize whether both of LOX-1 and the ApoA I antibody simultaneously through sandwich ELISA by using the LOX-1protein and the anti-ApoA I antibody in this examination. Therefore it was found that the prepared artificial recombinant protein simultaneously bound to LOX-1 and ApoA I antibody and is detected by the anti-ApoA I antibody. Accordingly, it was found that the preparation of the reference standard, which was stable and was able to be repeatably manufactured, was successful.

The fusion protein used for the reference standard for the measurement of the high-density lipoprotein, the nucleic acids or the vector or the cells for preparing the fusion protein, and the method for measuring the high-density lipoprotein and the measurement kit thereof, are explained in detail. The modified HDL can be accurately, simply and promptly detected and determined with excellent repeatability according to the present invention.

Since the measurement of the modified HDL can detect not only the amount thereof but also quality thereof, it will be the standard measurement method at some future date, as well as the measurement of HDL and LDL in the blood which are used as the indexes for a medical check-up.

According to the measurement of the modified HDL, the risk evaluation method for the arteriosclerotic diseases or the cardiac diseases such as the arteriosclerosis and the thrombogenesis etc. which has been missed out up to now, can be provided. And it can be used for the primary prophylaxis, the clinical examination, the investigation of the treatment policy, the medical treatment, the assessment of the effect of the medical treatment, and the secondary prophylaxis of the life style related diseases such as the arteriosclerotic diseases or the cardiac diseases etc.

INDUSTRIAL APPLICABILITY

The fusion protein of the present invention is useful as the reference standard for the method and kit of accurately measuring the high-density lipoprotein with excellent repeatability and reliability. The nucleic acids, the vector and the cells for producing the high-density lipoprotein are used for preparing the high-density lipoprotein.

The present invention of the method and kit of accurately measuring the high-density lipoprotein with excellent repeatability and reliability by using the fusion protein are used for obtaining the important information when accomplishing the prophylaxis or medical treatment for the arteriosclerotic diseases or the cardiac diseases etc.

What is claimed is:

1. A fusion protein comprising SEQ ID NO: 1.
2. A nucleic acid sequence encoding the fusion protein according to claim 1.
3. A vector comprising the nucleic acid sequence according to claim 2.
4. A cell comprising the vector according to claim 3.
5. A method for measuring a modified high-density lipoprotein in a test sample through binding of the modified high-density lipoprotein to LOX-1 and an anti-APOA I antibody, wherein, using the fusion protein according to claim 1 as a reference standard for the modified high-density lipoprotein, the reference standard and the modified high-density lipoprotein in the test sample are determined by comparison with the reference standard through an optical detection and/or radiation dosage detection.
6. A measurement kit for measuring a modified high-density lipoprotein in a test sample through bonding the modified high-density lipoprotein to LOX-1 and an anti-ApoA I antibody, the measurement kit comprising:
   the fusion protein of claim 1 as a reference standard for the modified high-density lipoprotein, to be measured through optical detection and/or radiological detection.
7. The measurement kit according to claim 6, further comprising LOX-1 and/or an anti-ApoA I antibody.

\* \* \* \* \*

SEQUENCE LISTING

```
<160> NUMBER OF SEQ ID NOS: 9

<210> SEQ ID NO 1
<211> LENGTH: 516
<212> TYPE: PRT
<213> ORGANISM: Artificial Sequence
<220> FEATURE:
<223> OTHER INFORMATION: designed peptide

<400> SEQUENCE: 1

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Val Ser Gly Phe Asp Phe Ser
        35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Ser Ser Thr Ile Asn Phe Thr Pro
65                  70                  75                  80

Ser Leu Lys Asp Lys Phe Ile Val Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Asn Asp Val Leu Leu Gly Ala Met Asp Tyr Trp Gly
        115                 120                 125

Gln Gly Thr Ser Val Thr Val Ser Ser Gly Gly Gly Ser Gly Gly
    130                 135                 140

Gly Gly Ser Gly Gly Gly Ser Asp Val Leu Met Thr Gln Thr Pro
145                 150                 155                 160

Leu Ser Leu Pro Val Ser Leu Gly Asp Gln Ala Ser Ile Ser Cys Arg
```

```
                165                 170                 175
Ser Ser Gln Thr Ile Val His Ser Asn Gly Lys Thr Tyr Leu Glu Trp
            180                 185                 190
Tyr Leu Gln Lys Pro Gly Gln Ser Pro Lys Leu Leu Ile Tyr Lys Val
        195                 200                 205
Ser Asn Arg Phe Ser Gly Val Pro Asp Arg Phe Ser Gly Ser Gly Ser
    210                 215                 220
Gly Thr Asp Phe Thr Leu Lys Ile Ser Arg Val Glu Ala Glu Asp Leu
225                 230                 235                 240
Gly Val Tyr Tyr Cys Phe Gln Gly Ser His Val Pro Leu Thr Phe Gly
            245                 250                 255
Ala Gly Thr Lys Leu Glu Leu Lys Gly Gly Gly Ser Gly Gly Gly
        260                 265                 270
Gly Ser Gly Gly Gly Gly Ser Pro Trp Asp Arg Val Lys Asp Leu Ala
    275                 280                 285
Thr Val Tyr Val Asp Val Leu Lys Asp Ser Gly Arg Asp Tyr Val Ser
    290                 295                 300
Gln Phe Glu Gly Ser Ala Leu Gly Lys Gln Leu Asn Leu Lys Leu Leu
305                 310                 315                 320
Asp Asn Trp Asp Ser Val Thr Ser Thr Phe Ser Lys Leu Arg Glu Gln
            325                 330                 335
Leu Gly Pro Val Thr Gln Glu Phe Trp Asp Asn Leu Glu Lys Glu Thr
        340                 345                 350
Glu Gly Leu Arg Gln Glu Met Ser Lys Asp Leu Glu Glu Val Lys Ala
        355                 360                 365
Lys Val Gln Pro Tyr Leu Asp Asp Phe Gln Lys Lys Trp Gln Glu Glu
    370                 375                 380
Met Glu Leu Tyr Arg Gln Lys Val Glu Pro Leu Arg Ala Glu Leu Gln
385                 390                 395                 400
Glu Gly Ala Arg Gln Lys Leu His Glu Leu Gln Glu Lys Leu Ser Pro
            405                 410                 415
Leu Gly Glu Glu Met Arg Asp Arg Ala Arg Ala His Val Asp Ala Leu
        420                 425                 430
Arg Thr His Leu Ala Pro Tyr Ser Asp Glu Leu Arg Gln Arg Leu Ala
        435                 440                 445
Ala Arg Leu Glu Ala Leu Lys Glu Asn Gly Gly Ala Arg Leu Ala Glu
    450                 455                 460
Tyr His Ala Lys Ala Thr Glu His Leu Ser Thr Leu Ser Glu Lys Ala
465                 470                 475                 480
Lys Pro Ala Leu Glu Asp Leu Arg Gln Gly Leu Leu Pro Val Leu Glu
            485                 490                 495
Ser Phe Lys Val Ser Phe Leu Ser Ala Leu Glu Glu Tyr Thr Lys Lys
        500                 505                 510
Leu Asn Thr Gln
        515

<210> SEQ ID NO 2
<211> LENGTH: 28
<212> TYPE: DNA
<213> ORGANISM: Artificial Sequence
<220> FEATURE:
<223> OTHER INFORMATION: forward primer

<400> SEQUENCE: 2
caccatgaaa gctgcggtgc tgaccttg                                        28
```

<210> SEQ ID NO 3
<211> LENGTH: 25
<212> TYPE: DNA
<213> ORGANISM: Artificial Sequence
<220> FEATURE:
<223> OTHER INFORMATION: reverse primer

<400> SEQUENCE: 3
ctgggtgttg agcttcttag tgtac                                  25

<210> SEQ ID NO 4
<211> LENGTH: 29
<212> TYPE: DNA
<213> ORGANISM: Artificial Sequence
<220> FEATURE:
<223> OTHER INFORMATION: forward primer

<400> SEQUENCE: 4
caccatggat tttgggctga ttttttta                               29

<210> SEQ ID NO 5
<211> LENGTH: 54
<212> TYPE: DNA
<213> ORGANISM: Artificial Sequence
<220> FEATURE:
<223> OTHER INFORMATION: reverse primer

<400> SEQUENCE: 5
accagagccg ccgccgccgc taccaccacc acctttcaac tccagcttgg tccc   54

<210> SEQ ID NO 6
<211> LENGTH: 58
<212> TYPE: DNA
<213> ORGANISM: Artificial Sequence
<220> FEATURE:
<223> OTHER INFORMATION: forward primer

<400> SEQUENCE: 6
agcggcggcg gcggctctgg tggtggtgga tcccggcatt tctggcagca agatgaac  58

<210> SEQ ID NO 7
<211> LENGTH: 27
<212> TYPE: DNA
<213> ORGANISM: Artificial Sequence
<220> FEATURE:
<223> OTHER INFORMATION: reverse primer

<400> SEQUENCE: 7
ctgggtgttg agcttcttag tgtactc                                27

<210> SEQ ID NO 8
<211> LENGTH: 25
<212> TYPE: DNA
<213> ORGANISM: Artificial Sequence
<220> FEATURE:
<223> OTHER INFORMATION: forward primer

<400> SEQUENCE: 8
ggatccacca ccaccagagc cgccg                                  25

<210> SEQ ID NO 9
<211> LENGTH: 25
<212> TYPE: DNA
<213> ORGANISM: Artificial Sequence
<220> FEATURE:

-continued

<223> OTHER INFORMATION: reverse primer

<400> SEQUENCE: 9
ccctgggatc gagtgaagga cctgg                                            25